(12) United States Patent
Smith et al.

(10) Patent No.: US 6,743,206 B1
(45) Date of Patent: Jun. 1, 2004

(54) ENDOSCOPIC NEEDLE

(75) Inventors: Kevin W. Smith, Coral Gables, FL (US); Juergen A. Kortenbach, Miami Springs, FL (US); Michael Sean McBrayer, Miami, FL (US)

(73) Assignee: Syntheon, LLC ( * ) Notice: Subject to any disclaimer, the term of this patent is extended or adjusted under 35 U.S.C. 154(b) by 0 days.

(21) Appl. No.: 09/520,291

(22) Filed: Mar. 7, 2000

(51) Int. Cl.$^7$ .............................................. A61M 5/178
(52) U.S. Cl. .................................................. 604/164.01
(58) Field of Search ................................. 604/164, 280, 604/282, 43, 264, 205, 493, 171, 198, 14, 202, 164.12, 164.01, 165.01

(56) References Cited

U.S. PATENT DOCUMENTS

| | | | |
|---|---|---|---|
| 4,327,711 A | 5/1982 | Takagi | 128/4 |
| 4,430,083 A | 2/1984 | Ganz et al. | 604/283 |
| 4,593,680 A | 6/1986 | Kubokawa | 128/4 |
| 4,763,667 A | 8/1988 | Manzo | 128/750 |
| 4,790,831 A | 12/1988 | Skribiski | 604/282 |
| 4,840,623 A | 6/1989 | Quackenbush | 604/280 |
| 4,950,232 A | 8/1990 | Ruzicka et al. | 604/43 |
| 4,967,732 A | 11/1990 | Inoue | 128/4 |
| 4,973,321 A | 11/1990 | Michelson | 604/280 |
| 5,005,755 A | 4/1991 | Takahashi et al. | 228/126 |
| 5,125,909 A | 6/1992 | Heimberger | 604/264 |
| 5,147,316 A | 9/1992 | Castillenti | 604/164 |
| 5,244,619 A | 9/1993 | Burnham | 264/173 |
| 5,279,280 A | 1/1994 | Bacich et al. | 128/6 |
| 5,279,541 A * | 1/1994 | Frayman et al. | 604/14 |
| 5,304,151 A * | 4/1994 | Kuracina | 604/198 |
| 5,334,169 A | 8/1994 | Brown et al. | 604/282 |
| 5,358,493 A | 10/1994 | Schweich et al. | 604/264 |
| 5,380,292 A | 1/1995 | Wilson | 604/164 |
| 5,404,887 A | 4/1995 | Prather | 128/772 |
| 5,406,939 A | 4/1995 | Bala | 128/4 |
| 5,465,710 A | 11/1995 | Miyagi | 600/139 |
| 5,496,292 A | 3/1996 | Burnham | 604/282 |
| 5,591,202 A | 1/1997 | Slater et al. | 606/205 |
| 5,601,533 A | 2/1997 | Hancke et al. | 604/164 |
| 5,601,588 A | 2/1997 | Tonomura et al. | 606/185 |
| 5,647,846 A | 7/1997 | Berg et al. | 604/493 |
| 5,681,296 A | 10/1997 | Ishida | 604/282 |
| 5,718,360 A | 2/1998 | Green et al. | 227/179 |
| 5,762,631 A | 6/1998 | Klein | 604/171 |
| 5,792,116 A * | 8/1998 | Berg et al. | 604/202 |
| 5,827,177 A | 10/1998 | Omeda et al. | 600/121 |
| 5,882,347 A | 3/1999 | Mouris-Laan | 604/280 |
| 5,885,508 A | 3/1999 | Ishida | 264/313 |
| 5,906,594 A * | 5/1999 | Scarfone et al. | 604/165.01 |
| 5,984,904 A | 11/1999 | Steen et al. | 604/264 |
| 6,083,202 A * | 7/2000 | Smith | 604/164.01 |
| 6,258,064 B1 * | 7/2001 | Smith et al. | 604/164.12 |

* cited by examiner

Primary Examiner—Henry Bennett
Assistant Examiner—Sabrina Dagostino
(74) Attorney, Agent, or Firm—Gordon & Jacobson, P.C.

(57) ABSTRACT

An endoscopic needle assembly has an inner tube formed from a close-wound coil of wire surrounded by a sheath, an outer tube surrounding the inner tube such that the inner tube can move longitudinally relative to the outer tube, a needle joined to a distal end of the inner tube, and a two piece handle having a first handle piece attaching to the inner tube and a second handle piece attaching to the outer tube. A safety shield, formed from a plurality of hinged petals, is built onto the distal end of the outer tube to protect an endoscope from inadvertent penetration by the needle.

5 Claims, 9 Drawing Sheets

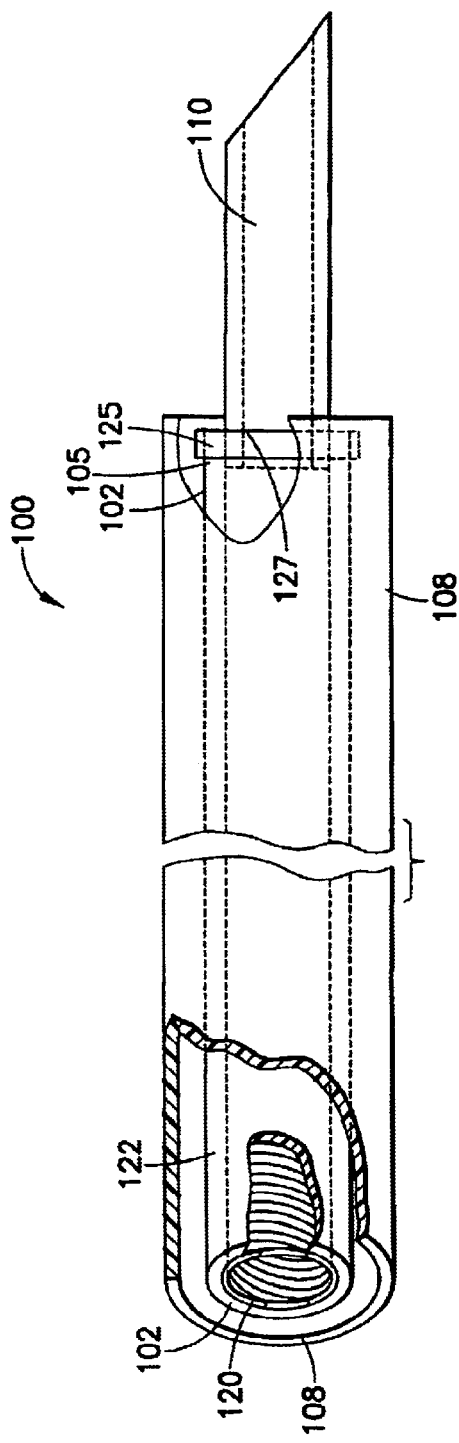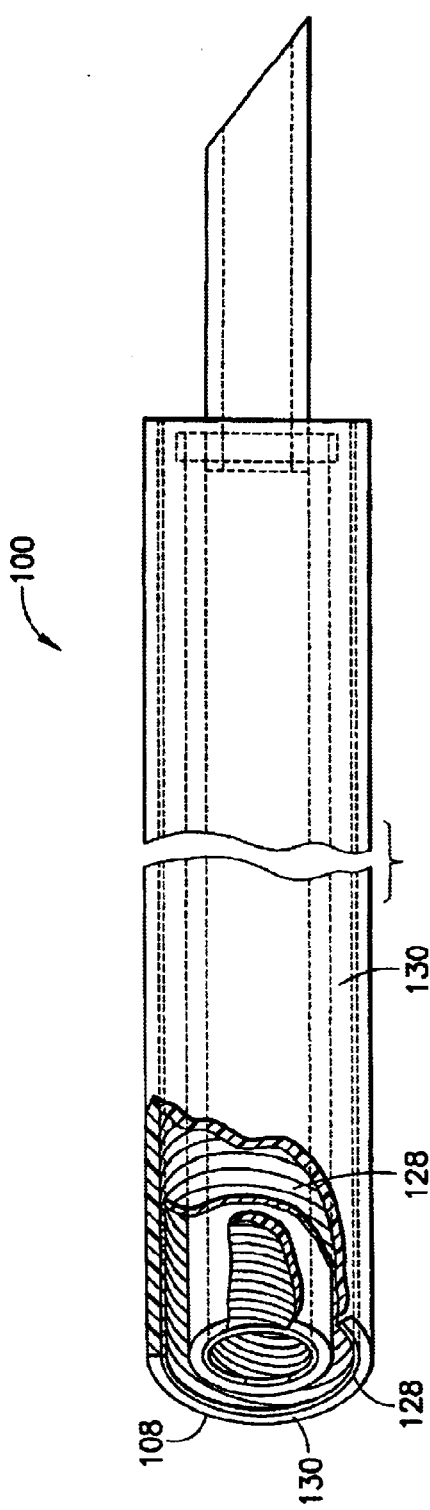

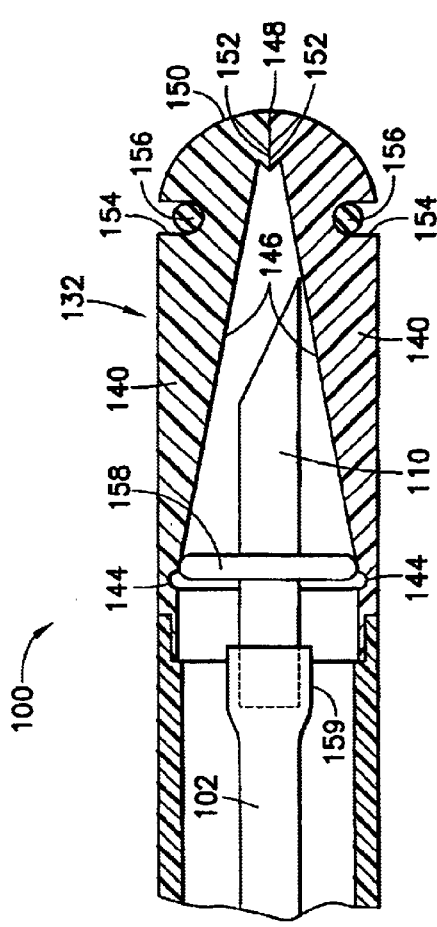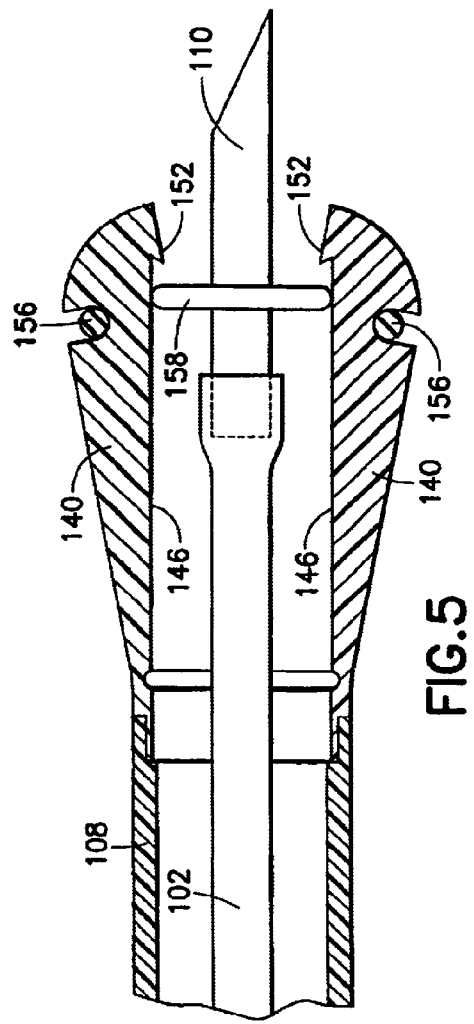

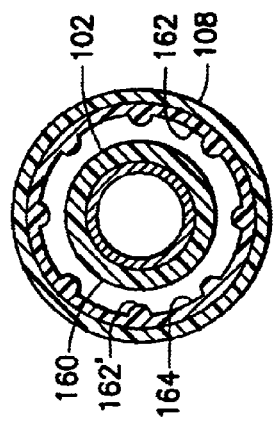
FIG.7a
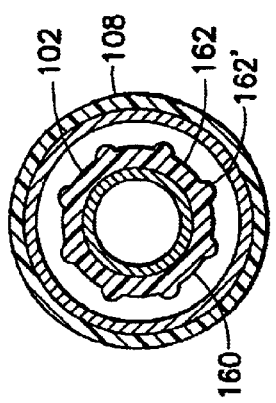
FIG.7b
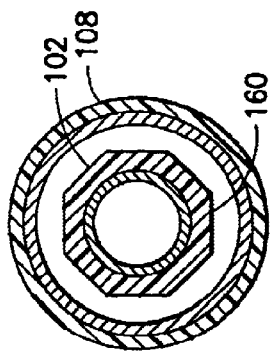
FIG.7c
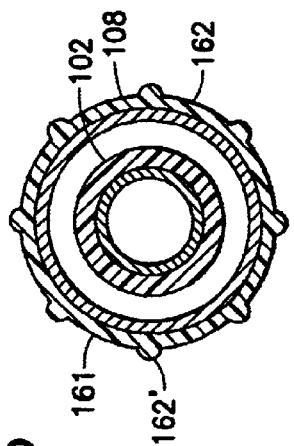
FIG.7d
FIG.7e
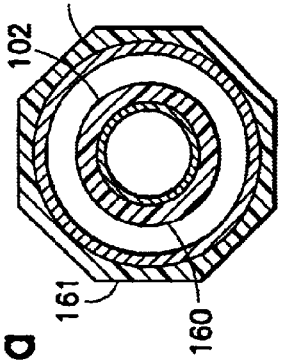
FIG.7f
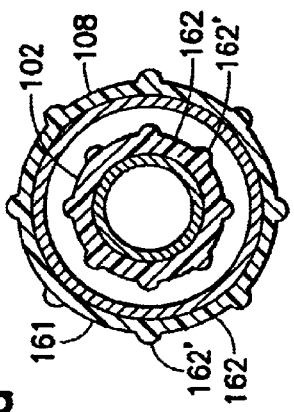
FIG.7g
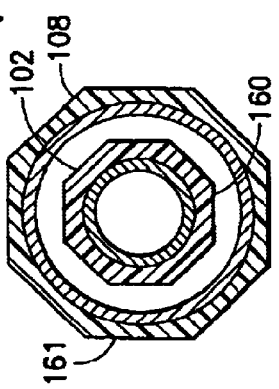
FIG.7h
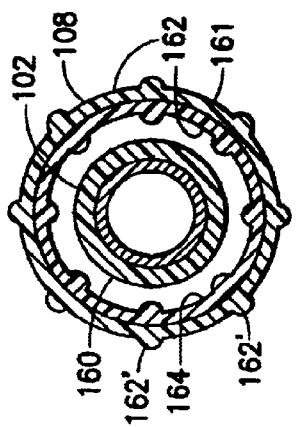

ENDOSCOPIC NEEDLE

BACKGROUND OF THE INVENTION

1. Field of the Invention

This invention relates broadly to surgical instruments. More particularly, this invention relates to endoscopic instruments, and particularly endoscopic needles.

2. State of the Art

Endoscopic needle assemblies are used with flexible endoscopes to inject fluids under endoscopic visualization in body structures such as the esophagus, the colon, and the stomach. For example, when removing polyps from within the colon, it is customary to inject saline solution into the tissue surrounding and underlying a polyp in order to "raise" the polyp thereby facilitating excision by means of forceps or snares. Visible dyes and radiological contrast dyes are sometimes injected to mark the location of areas explored endoscopically so that the structures can be located during subsequent procedures. Also, sclerosing agents are sometimes injected into vascular structures, such as esophageal varicoceles, in order to cause clotting and to necrose the tissue so that it can be reabsorbed by the body.

Such needle assemblies generally consist of a needle, an inner flexible tube, a flexible outer tube, a handle assembly and an injection syringe. The inner flexible tube provides a fluid pathway, and is surrounded by the loose-fitting flexible outer tube. The needle is connected to the distal end of the inner tube by use of adhesives, a stainless steel crimp band, or both, and the handle assembly is connected to the proximal end of the inner tube. Attached to the handle is an injection syringe, which supplies fluid to the fluid pathway of the inner tube when a plunger of the syringe is pushed. The inner tube is designed for the dual purpose of conducting fluids injected by a syringe located at the handle to the tissue surrounding the needle and for imparting motion produced at the handle to the needle. The handle assembly permits the user to move the inner tube in and out relative to the outer tube, thus retracting the needle into the outer tube or extending it beyond the distal tip of the outer tube. The outer tube is generally formed from a relatively flexible plastic polymer material such as PTFE or FEP. Sometimes the outer tube is also fitted with a band of stainless steel to reinforce its distal tip. The inner tube is generally formed from PTFE.

The needle assembly is designed to be inserted and fed into a smooth cylindrical working channel of an endoscope. In order to make the needle assembly flexible enough to negotiate the curves of an endoscope during use and to allow free motion of the needle assembly within the working channel of the endoscope, it is desirable to make the outer tube and the inner tube from a relatively flexible plastic polymer material such as PTFE or FEP. When the needle assembly is positioned properly within the endoscope, the needle of the needle assembly can be extended through a distal port in the endoscope by application of force on the handle of the needle assembly. When the operator applies the actuating force to the handle to extend the needle, a compressive force is applied to the inner tube, and a reactive tensile force is applied to the outer tube. Typically, the plastic inner tube is compressed and shortened and the plastic outer tube is stretched and elongated. This distortion causes the relative motion of the needle and the distal end of the outer tube to be sluggish and less than the full motion imparted to the handle on the proximal end of the device. Further, because of friction between the inner tube and outer tube, the motion of the needle relative to the distal tip of the outer tube is not immediate and direct; i.e., the force is not immediately and directly applied to the endoscopic needle assembly because the flexible polymer materials of the inner tube and the outer tube have some degree of elasticity in compression and tension and the force applied by the actuating handle is initially absorbed by the plastic material itself before it is translated into a positive and certain motion of the distal end of the endoscopic needle assembly.

Several problems result from the poor transmission of translational motion from handle to needle. First, the user must be able to move the endoscopic needle assembly relative to the endoscope's working channel (a lumen adapted to receive endoscopic instruments therethrough) in order to position the needle relative to the end of the endoscope and to stick the needle into the desired tissue. The compressiveness of the standard plastic outer tube and its friction relative to the endoscope's working channel and against the inner tube works against the ability of the user to precisely move the assembly in and out of the working channel. Second, it is difficult or impossible to push the needle into the tissue where an injection is desired by means of relative motion of the needle and the outer tube. Hence, the outer tube must be moved relative to the endoscope or the endoscope must be moved within the patient to effect the desired injection. Third, since the motion of the needle relative to the distal tip of the outer tube is not positive and certain, it is possible for the needle to move to an extended position when such is not desired. For example, it is possible for the needle to advance beyond the distal tip of the outer tube while the needle assembly is still within the working channel of the endoscope, which can result in internal damage to the endoscope and to the needle itself.

U.S. Pat. No. 5,601,588 to Tonomura et al. shows an endoscopic needle assembly in which the inner tube is made of metal, e.g., stainless steel or a super-elastic alloy, in order to minimize the compression in the inner tube. The needle may be formed integrally with the metallic inner tube or made as a separate part and attached to it. While the Tonomura et al. device offers an improvement to the standard all plastic construction, it also has several disadvantages. First, the stainless steel inner tube is stiffer than desired. The inner tube can be kinked if bent too tightly, and will take a permanent set if flexed beyond its elastic limit, as might be the case when the endoscope is tightly flexed while negotiating a tortuous colon or when being retroflexed. Second, a super-elastic alloy tube construction is prohibitively expensive for the intended general endoscopic use. Third, Tonomura et al. specifically does not address several problems: (1) accidental exposure of the needle within the endoscope, (2) the need for improving the tensile stiffness of the outer tube, and (3) the need for reducing the friction of the outer tube within the working channel of the endoscope to improve the user's control of the endoscopic needle relative to the endoscope.

Other prior art exists relating to endoscopic needle devices, but none of the prior art teaches improvements in the relative motion of the inner tube and outer tube, nor in flexibility and kink resistance of the inner tube, nor in reducing friction between the outer tube and the working channel of the endoscope.

SUMMARY OF THE INVENTION

It is therefore an object of the invention to provide an endoscopic needle assembly with an improved inner tube with reduced compression and reduced likelihood of kinking resulting in better control of the needle from the endoscope handle.

It is another object of the invention to provide an endoscopic needle assembly having an outer tube with improved tensile stiffness, i.e., a relatively small amount of longitudinal stretching or compression caused by a given amount of tensile or compressive force, resulting in more direct control of the needle within the endoscope.

It is a further object of the invention to provide an improved endoscopic needle assembly with a safety shield by which accidental exposure of the needle within the endoscope is prevented.

It is an additional object of the invention to provide an endoscopic needle assembly with an improved outer tube having a friction reducing exterior surface such that friction is reduced between the outer tube and the working channel of the endoscope to improve the user's control of the endoscopic needle relative to the endoscope.

Another object of the invention is to provide an endoscopic needle assembly with an improved inner tube having a friction reducing exterior surface such that friction is reduced between the inner tube and the outer tube to improve the user's control of the endoscopic needle relative to the endoscope.

In accord with these objects which will be discussed in detail below, a first embodiment of an endoscopic needle assembly according to the invention generally includes an inner tube, an outer tube, a needle coupled to a distal end of the inner tube, and a handle assembly coupled to proximal ends of both the inner tube and the outer tube. The inner tube forms a fluid pathway or lumen connecting the needle with a syringe. The inner tube is formed from a low-friction material, such as high-density polyethylene, which is substantially non-elastic in tension and compression and yet is still considerably flexible. The outer tube, which is substantially non-elastic in tension and compression and yet is still considerably flexible, surrounds the inner tube such that the inner tube can move freely within the outer tube. The handle is designed such that it provides a convenient grip for the user, a connection for an injection syringe, and serves as a means for moving the inner tube axially relative to the outer tube.

According to a first preferred aspect of the first embodiment of the invention, the inner tube is formed having a tube-on-coil construction formed from a close-wound coil of stainless steel wire covered by a close fitting tube of a low-friction material, such as high-density polyethylene.

According to a second preferred aspect of the first embodiment of the invention, the outer tube is also formed having a tube-on-coil construction formed from a close-wound coil of wire covered by a close fitting tube of low-friction material.

According to a third preferred aspect of the first embodiment of the invention, a safety shield formed from a plurality of hinged petals is provided at the distal end of the outer tube to protect the endoscope from inadvertent penetration by the needle in the endoscope. The petals are held shut by an elastic element, but can be opened by application of a small force applied at the handle of the endoscopic needle assembly which moves the inner tube and needle relative to the outer tube and through the petals. When the endoscopic needle assembly is within the working channel of the endoscope, the petals cannot be expanded and the outer tube moves freely in and out of the working channel of the endoscope. When the petals are expanded, it is not possible to retract the outer tube back into the working channel of the endoscope; and thus the needle is prevented from contacting or penetrating the endoscope.

According to a fourth preferred aspect of the first embodiment of the invention, in order to reduce friction between the inner tube and the outer tube and/or between the outer tube and the working channel of the endoscope, the inner tube and the outer tube or combinations thereof are designed to have relatively different cross-sectional shapes.

Alternatively, the inner tube of the first preferred embodiment may be formed from a similar flexible low-friction material, such as high-density polyethylene, having a piece of a thin metal wire attached at a specific segment along the interior of the flexible inner tube. The piece of wire provides the segment of the inner tube with a measure of rigidity in tension and compression. The short length of wire may also be used to strengthen a segment of the inner tube which has a reduced diameter. Further, the alternate embodiment may also incorporate a first preferred aspect, a tube-on-coil construction outer tube; a second preferred aspect, a safety shield attached to the outer tube; and a third preferred aspect, an inner tube and an outer tube having relatively different cross-sectional shapes.

A second embodiment of the invention generally comprises a thin metal actuating wire, an outer tube connected to a syringe, a needle coupled to a distal end of the thin wire, and a handle coupled to proximal ends of the thin wire and outer tube. The thin metal actuating wire, which runs the full length within the flexible outer tube, is coupled to the needle and is used instead of an inner tube to communicate the motion imparted by the handle to the needle at the distal end of the endoscopic needle assembly. Proximal and distal sliding seals surround the thin wire and the needle, respectively, and effectively cause the outer tube to become an enclosed fluid channel, with the needle remaining in fluid communication with the syringe.

According to a first preferred aspect of the second embodiment of the invention, the outer tube is formed having a tube-on-coil construction formed from a close-wound coil of stainless steel wire covered by a close fitting tube of a low-friction material, such as high-density polyethylene. The outer tube provides a fluid pathway between the needle and a lumen of the syringe.

According to a second preferred aspect of the second embodiment of the invention, a safety shield is built onto the distal end of the outer tube to protect the endoscope from inadvertent penetration by the needle in the endoscope while the endoscopic needle assembly is within the working channel of the endoscope.

According to a third preferred aspect of the second embodiment of the invention, the outer tube may be formed having a non-circular cross-section which reduces the friction between the outer tube and the working channel of the endoscope.

A third embodiment of the invention generally comprises an inner tube, an outer tube, a thin metal actuating wire, a handle and a needle. The thin metal actuating wire runs the full length of the flexible inner tube. It is coupled distally to the needle and proximally to the handle, and is used to communicate the motion imparted at the handle to the needle at the distal end of the endoscopic needle assembly. A syringe, attached to the endoscopic needle assembly, is in fluid communication with the inner tube and the needle. The syringe delivers fluid to the needle through a fluid pathway formed by the inner tube. Further, the third embodiment may also incorporate a first preferred aspect, a tube-on-coil construction outer tube, a second preferred aspect, a safety shield attached to the outer tube surrounding the needle, and a third preferred aspect, an inner tube and an outer tube having a non-circular cross-section.

With the above embodiments and preferred aspects the following advantages are attained: improved tensile and compressive strength of the inner and outer tube which improves control of the endoscopic needle assembly; reduced friction between the inner and outer tube, and between the outer tube and the working channel of the endoscope, both of which also improve control and maneuverability of the endoscopic needle; and reduced likelihood of inadvertent penetration of the needle into the endoscope.

Additional objects and advantages of the invention will become apparent to those skilled in the art upon reference to the detailed description taken in conjunction with the provided figures.

BRIEF DESCRIPTION OF THE DRAWINGS

FIG. 2 is an enlarged broken cut-away and partially sectional partially perspective view of the distal end of the endoscopic needle assembly of FIG. 1 incorporating a first preferred aspect;

FIG. 3 is an enlarged broken cut-away and partially sectional partially perspective view of the distal end of the endoscopic needle assembly of FIG. 1 incorporating a second preferred aspect;

FIG. 4 is an enlarged broken cut-away view of a third preferred aspect of the endoscopic needle assembly of FIG. 2, illustrating a safety shield in a closed configuration;

FIG. 5 is a view similar to FIG. 4 with the safety shield shown in an open configuration;

FIGS. 7a–7h show cross-sections of eight embodiments of the fourth preferred aspect of the endoscopic needle assembly of FIG. 3;

DETAILED DESCRIPTION OF THE PREFERRED EMBODIMENTS

Figure 1:
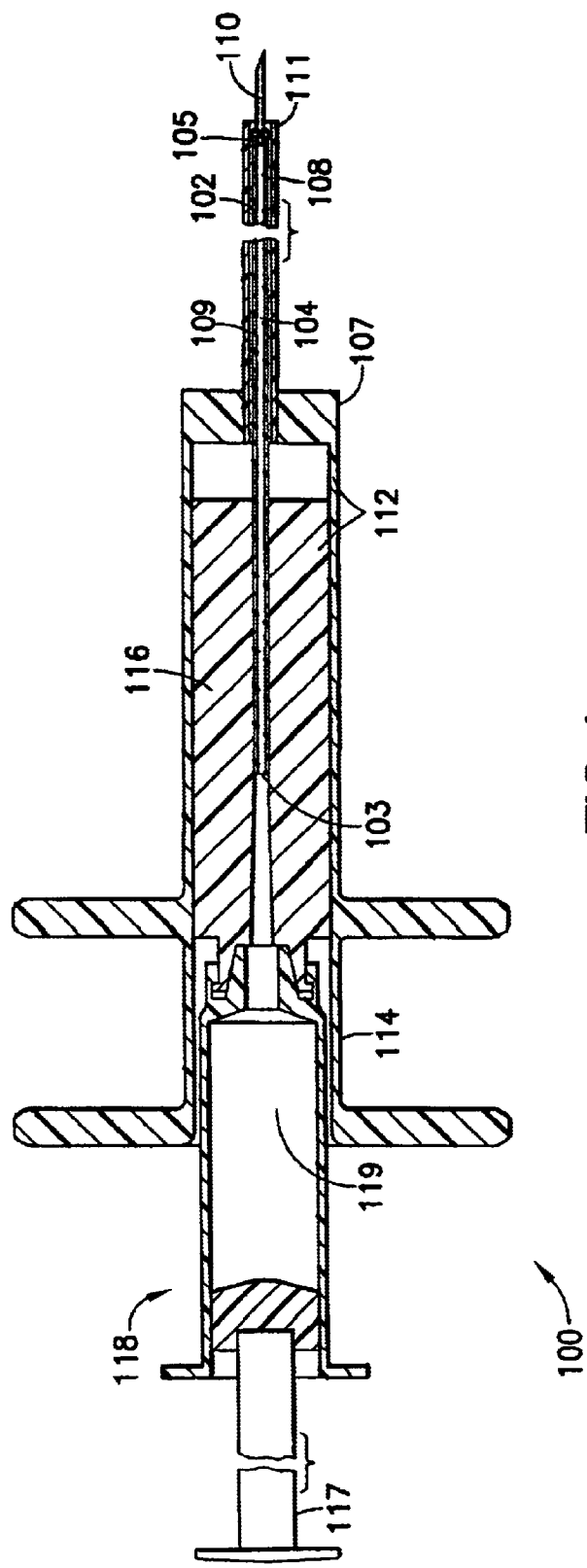
FIG. 1 is a broken sectional view of a first embodiment of an endoscopic needle assembly according to the invention.
Figure 6A:
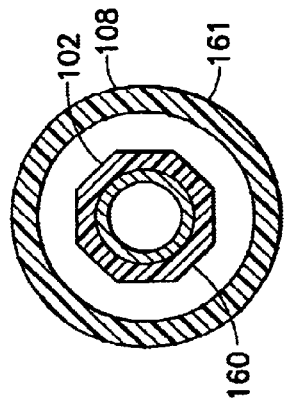
FIGS. 6a–6h show cross-sections of eight embodiments of the fourth preferred aspect of the endoscopic needle assembly of FIG. 2.
Figure 6B:
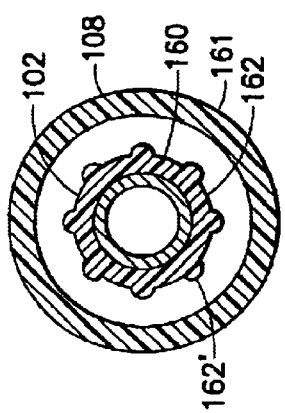
Figure 6C:
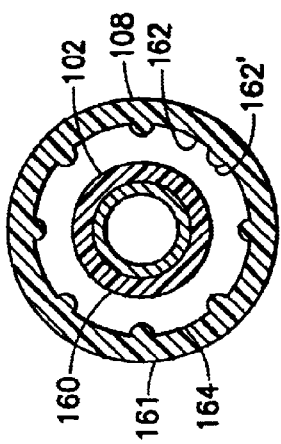
Figure 6D:
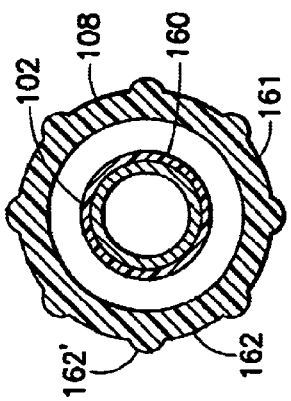
Figure 6E:
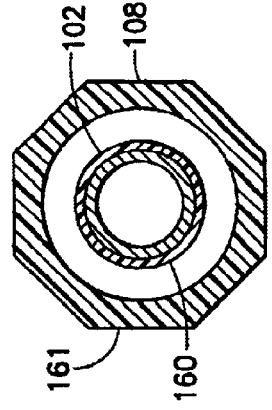
Figure 6F:
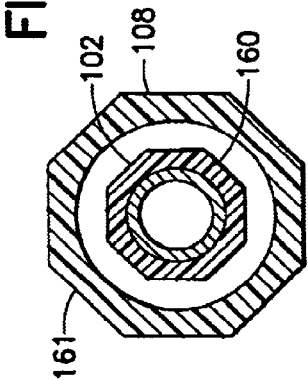
Figure 6G:
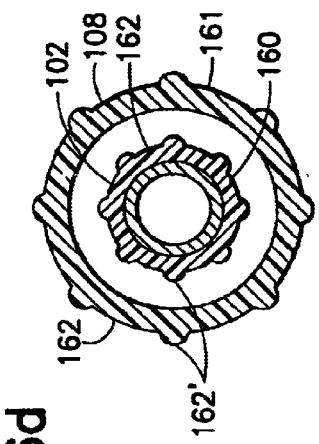
Figure 6H:
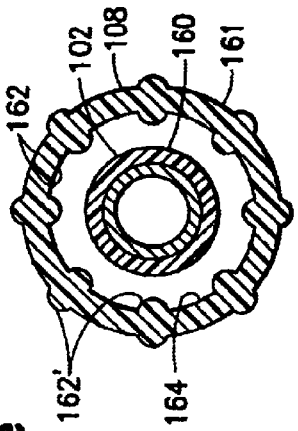

Turning now to FIG. 1, a first embodiment of an endoscopic needle assembly 100 is shown. The endoscopic needle assembly 100 has an inner tube 102 having a proximal end 103 and a distal end 105, an outer tube 108 having a proximal end 107 and a distal end 111, a needle 110 coupled to the distal end 105 of the inner tube 102, and a two piece handle assembly 112. The inner tube 102 has a lumen 104 defining a fluid pathway between a syringe 118 coupled to the handle assembly 112 and the needle 110. The outer tube 108 has a lumen 109 through which the inner tube 102 may be moved longitudinally within the outer tube 108. The two piece handle assembly 112 is formed having a stationary handle piece 114 attached to the proximal end 107 of the outer tube 108, and a movable handle piece 116 attached to the proximal end 103 of the inner tube 102. The stationary handle piece 114 provides a convenient grip for the user when maneuvering the endoscopic needle assembly within a working channel of an endoscope (not shown). The moveable handle piece 116 serves as a means for moving the inner tube 102 longitudinally relative to the outer tube 108. The syringe 118 has a reservoir 119 which is in fluid communication with the lumen 104 of the inner tube 102, and a plunger 117, which expels fluid (not shown) contained within the reservoir 119 of the syringe 118 into the fluid pathway 106 and through the needle 110.

Referring to FIG. 2 which shows a first preferred aspect of the first embodiment of the endoscopic needle assembly 100, the inner tube 102 is formed having a tube-on-coil construction from a first coil 120 of wire surrounded by a first sheath 122. The first sheath 122 is preferably composed of a low-friction material, such as high-density polyethylene. The first coil 120 is preferably made of flat stainless steel wire of approximately 0.004 inch thickness and 0.010 inch width, wound to form a close-wound coil with a 0.038 inch outside diameter. The first sheath 122 is preferably formed as an extruded tube of high-density polyethylene of between 0.001 and 0.01 inch thick and with an outside diameter of 0.046 inch. The first sheath 122 is preferably heat-shrunk onto the first coil 120. The stainless steel needle 110 is joined to the distal end 105 of the inner tube 102 by a crimp band 125, which is preferably formed from stainless steel. The crimp band 125 preferably has a chamfered distal edge 127. The outer tube 108 of the first embodiment 100 may be formed as a simple plastic tube from a high tensile strength polymer such as polyetherketone (PEEK); Halar (ECTFE), Nylon-6, or Nylon-12. The outer tube 108 preferably has an outer diameter of approximately 0.072 inches and inner diameter of approximately 0.054 inches.

Turning to FIG. 3, a second preferred aspect of the first embodiment 100 of the invention is shown. In the second preferred aspect, the outer tube 108 is also formed from a tube-on-coil construction wherein a second coil 128 is covered with a second sheath 130. The second coil 128 is preferably wound from flat stainless steel wire having a thickness of 0.010 inches and a width of 0.030 inches. The second sheath 130, which is preferably formed from extruded high-density polyethylene, preferably has a diameter of 0.072 inches and a 0.003 inch wall thickness. As with the inner tube construction, the second sheath 130 is preferably heat-shrunk onto the second coil 128.

Referring to FIG. 4, according to a third preferred aspect of the first embodiment of the invention 100, a safety shield 132 having a plurality of hinged petals 140 (preferably four but only two shown in the section view) is coupled to the outer tube 108 at or adjacent the distal end 111. The shield 132 protects the working channel of the endoscope from inadvertent penetration by the needle 110 as the endoscopic needle assembly 100 is maneuvered through the endoscope. The safety shield 132 is preferably formed from a stiff polymer plastic, such as polypropylene or nylon-12 and preferably sized to securely fit within (or about) the outer tube 108. A bonding agent is preferably used to secure the shield 132 to the distal end 111 of the outer tube 108. The proximal end of each petal 140 preferably includes a groove 144 to result in an area with increased flexibility; i.e., a living hinge. The interior of each petal 140 includes a ramp 146 which slopes from adjacent the hinge 144 toward a midpoint of the distal tip 150 of the shield 132. The ramp 146 distally terminates in a stop portion 152. The exterior of each petal includes a channel 154, together forming a circumferential channel. An elastic band 156, e.g., a SILASTIC O-ring, is positioned in the circumferential channel of the petals and biases the shield 132 into a closed configuration, as shown. A cam 158 is provided to the needle, preferably distal the juncture 159 of the inner tube 102 and the needle 110.

The dimensions of the shield 132 are such that the shield 132 is unable to open within the working channel of an endoscope. However, once the endoscopic needle assembly 100 is advanced distally beyond the working channel of the endoscope, the shield 132 is no longer constrained by the confines of the working channel of the endoscope.

Referring to FIG. 5, the petals 140 of the shield 132 may then be forced open by operating the moveable handle piece 116 (FIG. 1) to produce an actuating force extending the inner tube 102 distally within the outer tube 108 such that the cam 158 on the needle 110 rides on the ramps 146 of the petals 140, thereby forcing the petals open against the bias of the elastic band 156. The cam 158 cannot be extended past the stop portion 152 on the petals, thereby preventing the needle from extending too far beyond the outer tube 108. Since the outer surfaces of the petals 140, when open, diverge from each other, it is not possible to retract the outer tube 108 back into the working channel of the endoscope until the petals 140 are closed. When the needle 110 is retracted, the band 156 functions to restore the petals 140 of the shield into the closed configuration.

Referring now to FIGS. 6a–6h and FIGS. 7a–7h, cross-sections of a fourth preferred aspect of the first embodiment of the invention designed to reduce friction between two contacting surfaces are shown. Specifically, FIGS. 6a–6h show in cross-section the endoscopic needle assembly of FIG. 2; and FIGS. 7a–7h show in cross-section the endoscopic needle assembly of FIG. 3. In order to reduce friction between the inner tube 102 and the outer tube 108 and/or the outer tube 108 and the working channel of the endoscope, either or both the inner tube 102 and the outer tube 108 is formed having a non-circular cross-section such that there are fewer points of contact between the contacting surfaces of the tubes. For example and not by way of limitation as shown in FIGS. 6a, 6d, 6f, 7a, 7d, and 7f, either of the tubes can be extruded with a respective outer surface 160, 161 having a polygonal shape, e.g., octagonal.

Alternately, as shown in FIGS. 6b, 6e, 6g, 6h, 7b, 7e, 7g, and 7h, one or both of the outer surface 160 of the inner tube 102 and the outer surface 161 of the outer tube 108 could be extruded with a plurality of preferably evenly spaced grooves 162 or ridges 162' to minimize the inner tube 102 contact with the outer tube 108 and the outer tube 108 contact with the working surface of the endoscope. For example and not by way of limitation, the plurality of grooves 162 or ridges 162', could be each 0.003 inch wide and 0.002 inches high and substantially evenly spaced around the periphery of the tube.

Alternately, as shown in FIGS. 6c, 6h, 7c, and 7h, to minimize contact between the inner tube 102 and the outer tube 108, an inner surface 164 of the outer tube 108 could be extruded with a similar plurality of preferably evenly spaced grooves 162 or ridges 162'. Friction reduction by reducing contact between elements is especially noticeable when utilizing soft materials, such as PTFE and polyethylene.

Figure 8:
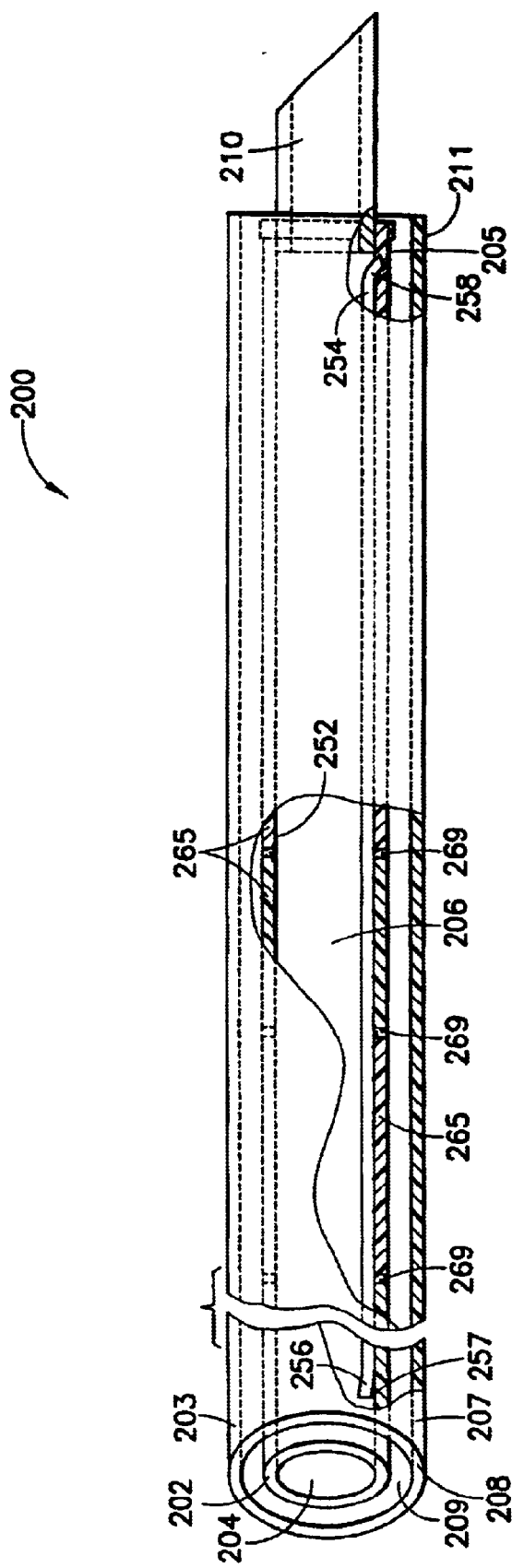
FIG. 8 is an enlarged broken partially sectional partially perspective view of the distal end of an alternate embodiment of the endoscopic needle assembly of FIG. 1.

Referring to FIG. 8, an alternate first embodiment 200 of the endoscopic needle assembly 100, similar to the first embodiment (in which like parts have reference numerals incremented by 100), is shown. The alternate embodiment 200 includes an inner tube 202 having a proximal end 203 and a distal end 205 and a lumen 204 formed by an interior wall 252 which creates a fluid pathway 206. A needle 210 is coupled to the distal end 205 of the inner tube 202. An outer tube 208 having a proximal end 207 and a distal end 211 forms a lumen 209 through which the inner tube 202 is longitudinally movable relative to the outer tube 208. The alternate embodiment 200 also has a handle assembly (not shown) formed in two pieces having a stationary piece connected to the outer tube 208 and a movable piece connected to the inner tube 202. In accord with the alternate embodiment, a piece of wire 254 has a proximal end 256 attached to the handle itself (not shown), trapped in the inner tube-to-handle bond (not shown), or attached to a proximal portion of the inner tube 202, for example by a crimp joint, a heat bonding process or an adhesion bond 257. The wire 254 preferably extends along substantially the entire length of the inner tube 202. A distal end 258 of the wire 254 is attached to the interior wall 252 preferably at the distal end 205 of the inner tube 202. The wire is preferably made from 304 stainless steel, and preferably has a diameter of 0.004 inch to 0.025 inch, and more preferably a diameter of 0.010 inch. The piece of wire 254 provides a measure of compressive and tensile strength and longitudinal stability along the inner tube 202 while allowing the inner tube 202 to remain otherwise relatively flexible. In the segment of the inner tube 202 having the piece of wire 254, the actuating force applied at the handle to move the inner tube 202 and needle 210 longitudinally in and out of the outer tube 202 is born primarily by the piece of wire 254. The outer tube 208 of the alternate embodiment may be formed from a high yield strength/high tensile strength polymer material or as a tube-on-coil construction as described in FIG. 3. The inner tube 202 of the alternate embodiment may be formed from a flexible polymer material or a combination of multiple segments of flexible polymer materials joined together.

Additionally, the inner tube 202 may be formed as a plurality of segments 265 formed from any of a variety of stiffer, less flexible materials, or formed having thicker cross-sections 267 which suffice to transmit the actuating force from the handle assembly 212 to the needle 210. In such a construction it may be necessary to have joints 269 where the multiple segments 265 of the inner tube 202 are joined to one another. The joints are preferably made by welding the segments 265 together (melting and forcing together) or by bonding with adhesion. Alternatively, the inner tube 202 may be extruded in a manner that provides a transition along its length from a material having a first durometer to another material having a different durometer. Further, the inner tube 202 may taper in thickness or a diameter of the inner tube 202 may narrow distally.

Figure 9:
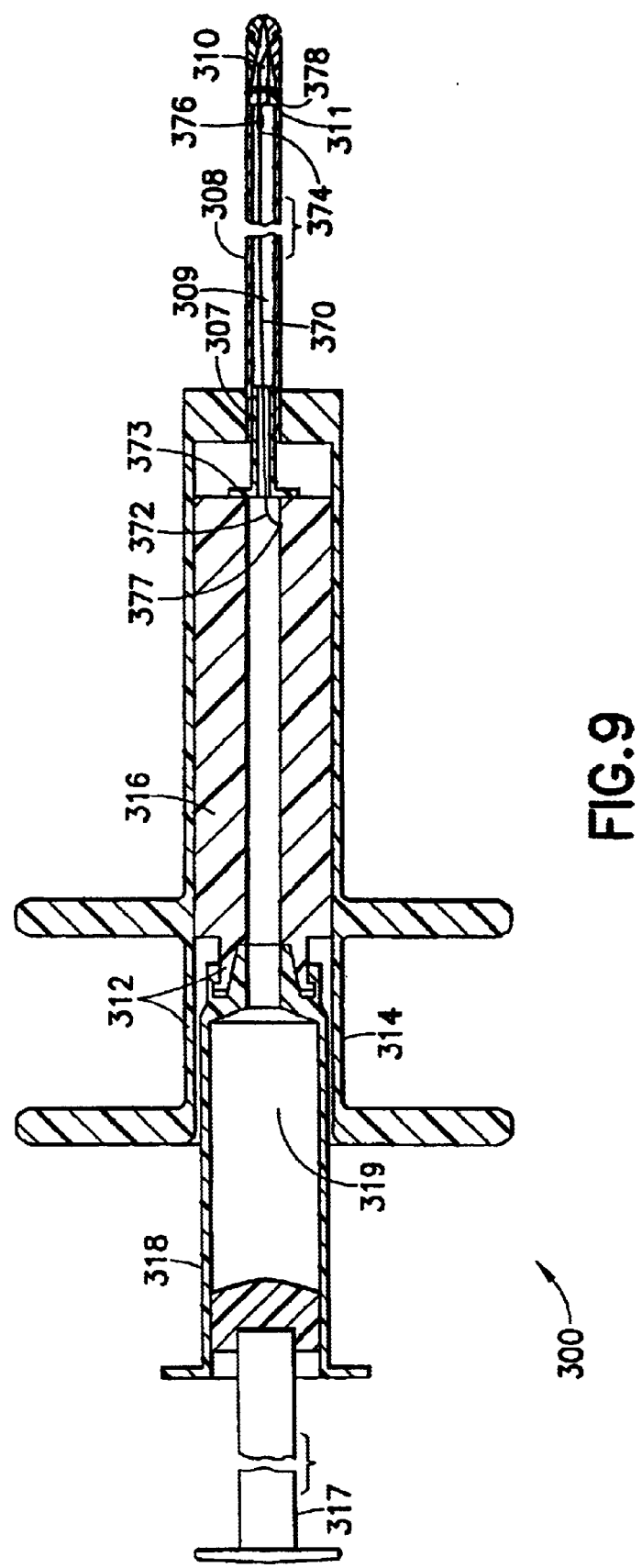
FIG. 9 shows a broken sectional view of a second embodiment of an endoscopic needle assembly according to the invention.
Figure 10:
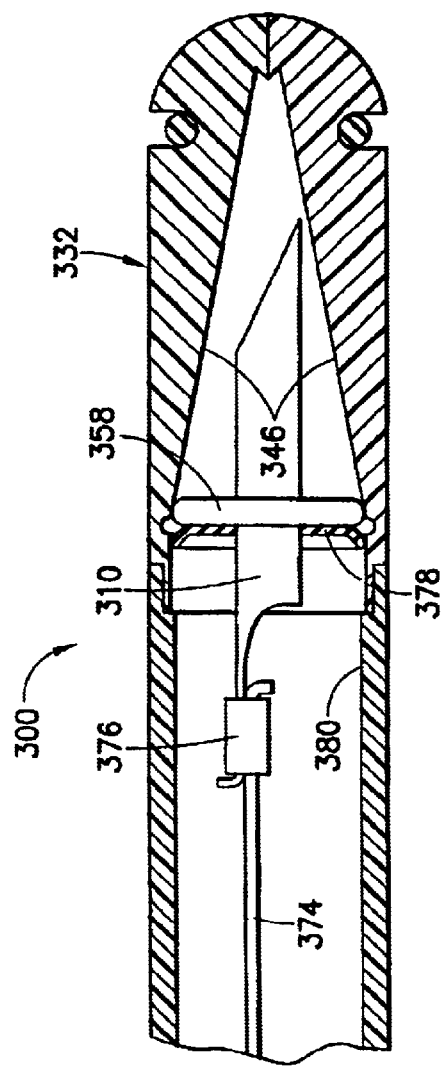
FIG. 10 is an enlarged broken cut-away view of the distal end of a second embodiment of the endoscopic needle assembly of FIG. 9 incorporating a first and second preferred aspect.

Referring to FIGS. 9 and 10, a second embodiment of an endoscopic needle assembly 300, substantially similar to the first embodiment (with like parts having reference numbers incremented by 200 relative thereto), is shown. The endoscopic needle assembly 300 has a tube 308 having a proximal end 307 and a distal end 311 and forming a lumen 309 which defines as a fluid pathway, a wire 370 having a proximal end 372 and a distal end 374 running within the tube 308, a two piece handle assembly 312, and a syringe 318 having a reservoir 319. The syringe 318 has a plunger 317 which expels fluid (not shown) contained within the reservoir 319 of the syringe 318 into the fluid pathway 309 of the tube 308. The handle assembly 312 has a stationary handle piece 314 connected to the proximal end 307 of the tube 308 and a moveable handle piece 316 coupled to the proximal end 372 of the wire 370. A fluid seal connector 373 extends around a proximal portion of the wire 370 and is coupled to the distal end of the movable handle piece 316 (e.g., by adhesive bond). The seal connector 373 is slidably movable within the proximal end of the tube 308. As such, when the movable handle piece 316 is moved relative to the stationary handle piece 314, a fluid conduit is maintained between the reservoir 319 and the fluid pathway 309. The distal end 374 of the wire 370 connects to a needle 310 which has its bore in fluid communication with the fluid pathway 309 of the tube 308 and the reservoir 319 of the syringe 318. The wire 370, which is substantially inelastic in tension and compression (but otherwise flexible), relays movements actuated at the moveable handle piece 316 to the needle 310. The proximal end 372 of the wire 370 is attached to the moveable handle piece 316 preferably by adhesion bonding, a crimp joint, or a welded joint. A distal end 374 of the wire 370 is connected to the needle 310 by means of a crimp band 376, a weld, or by adhesion bonding.

As shown in FIG. 10, the second embodiment of the endoscopic needle assembly 300 can be formed having a protective shield 332 surrounding the needle 310 as described with reference to FIGS. 4 and 5. A cam 358 about the needle 310 operates to force open the shield 332. A sliding seal 378, preferably positioned at the proximal side of the cam, extends between the needle 310 and the interior wall surface 380 of the tube 308. As such, fluid forced through the fluid pathway 306 is prevented from exiting the distal end of the tube around the needle and is directed through the needle. Moreover, as the needle 310 is moved though the shield 332, the seal will be in contact with the ramps 346 of the shield and maintains its sealing integrity.

Figure 11C:
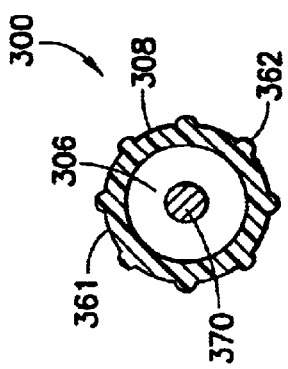
FIGS. 11a–11c show cross-sections of three embodiments of the third preferred aspect of the endoscopic needle assembly of FIG. 10.
Figure 11B:
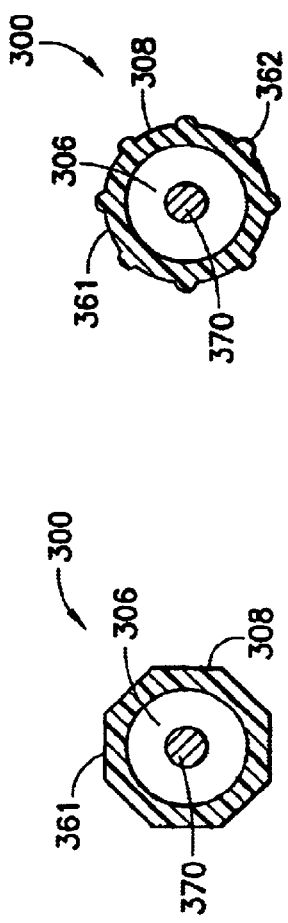
Figure 11A:
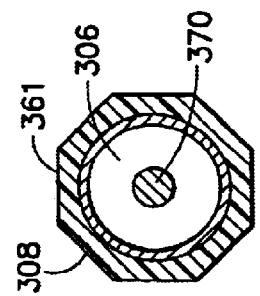

Referring now to FIGS. 11a–11c, the second embodiment of the endoscopic needle assembly 300 may be provided with an outer tube 308 having an outer surface 361 having a non-circular cross-section. The non-circular cross-section may be formed by either shaping the outer surface 361 of the outer tube 308 (such as into an octagon as shown in FIGS. 11a–11b) or by forming a plurality of grooves or ridges 362 on the outer surface 361 (as shown in FIG. 11c).

Figure 12:
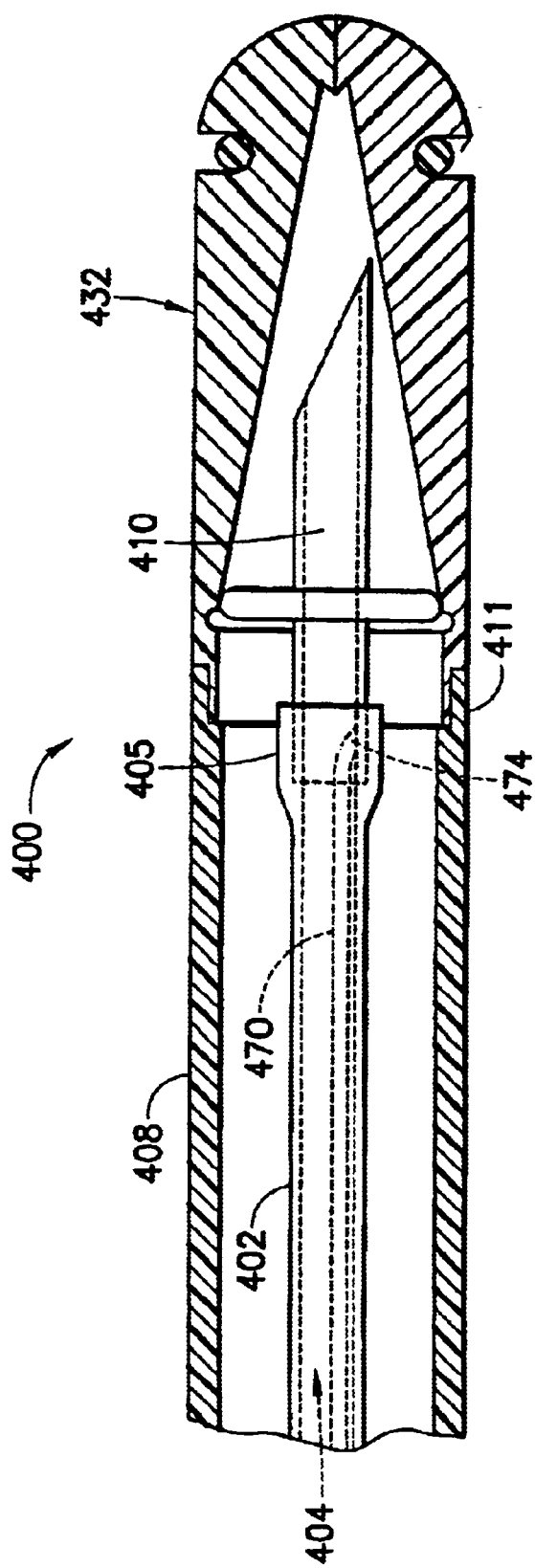
FIG. 12 is an enlarged broken cut-away view of the distal end of a third embodiment of the endoscopic needle assembly of FIG. 1 incorporating a first preferred aspect.

Referring to FIG. 12, a third embodiment of the endoscopic needle assembly 400 is shown. The endoscopic needle assembly 400 includes an inner tube 402 having a distal end 405 and a lumen 404 defining a fluid pathway, a needle 410 attached to the distal end 405 of the inner tube 402, an actuating wire 470 extending through the lumen 404 of the inner tube 402 and having a distal end 474 coupled to the needle 410 (e.g., via a weld), an outer tube 408 surrounding the inner tube 402, and a two piece handle (not shown) having a stationary handle piece which attaches to the outer tube 408 and a moveable handle piece which attached to the proximal ends of the inner tube 402 and the actuating wire 470 in a manner similar to that of the first and second embodiments. The third embodiment 400 may also include a safety shield 432 attached to a distal end 411 of the outer tube 408. Further, as with the inner tube 102 and outer tube 108 of the first embodiment of the endoscopic needle assembly 100, the inner tube 402 and the outer tube 408 of the third embodiment of the endoscopic needle assembly 400 may be formed from tube-on-coil construction or from a flexible polymer material and may also be formed having friction reducing aspects including non-circular cross-sections.

There have been described and illustrated herein several embodiments of an endoscopic needle assembly. While particular embodiments of the invention have been described, it is not intended that the invention be limited thereto, as it is intended that the invention be as broad in scope as the art will allow and that the specification be read likewise. Thus, while a typical coil wire having a specific thickness and width was disclosed, the coil wire may have a preferred thickness ranging from 0.001 inches to 0.015 inches and have a preferred width ranging from 0.001 inches to 0.050 inches. Also, while it was disclosed in particular embodiments that the first and second coils of wire forming the tube-on-coil construction of the inner tube and outer tube respectively were preferably formed from flat wire, it is understood that the coils can alternatively be made from round wire having a preferred diameter ranging from 0.001 inches to 0.025 inches. In addition, while specific coil diameters were disclosed, it is understood that the coils can be formed having other diameters such that when coated with a sheath, a first coil is slidable within a second coil and a second coil is slidable within the working channel of an endoscope. Furthermore, while it is preferable that stainless steel wire be used to form the coils, it is understood that wire formed from other alloys or metals can be used as well. While it was disclosed that the sheaths were preferably formed from high-density polyethylene having a particular thickness, it is understood that the sheaths could be formed from any flexible, low-friction polymer, such as nylon, PTFE, FEP, urethane, low-density polyethylene, ECTFE, polycarbonate, or polyacetal in other thicknesses. Also, while the sheath is preferably heat-shrunk to the coil, it is understood that the sheath may also be pressure-expanded then slipped over the coil and allowed to relax to form a "shrunk-on" jacket. In addition, while a needle preferably formed from stainless steel has been disclosed, it will be appreciated that other materials may be used as well. For example and not by way of limitation, the needle can be made of other alloys typically used in medical devices such as aluminum bronze, titanium, and chromium-cobalt alloys, or from any of the customary super-elastic alloys, including nickel-titanium, copper-zinc, and palladium-gold. Furthermore, while it was disclosed that the needle may be joined to the inner tube by means of a crimp band, it is understood that other methods of joining the needle and the inner tube may be used including but not limited to adhesives, heat-bonding, hot-melt adhesive or combinations of these and a crimp band. Moreover, while one type of handle was disclosed, it is understood by those in the art that other types of handles having other functional aspects may be used instead. For example and not by way of limitation, the following may be used: a three-ring handle (two finger rings on a sliding member and one thumb ring on a central member, so that moving the finger rings relative to the thumb ring causes relative motion of the inner and outer tubes); a spool-on-shaft handle (a spool with a flange at one end or at both ends sliding over a central shaft, so that moving the flanged spool along the central shaft causes relative motion of the inner and outer tubes); and a scissors-handle (two handles, each with a ring for fingers or thumb at one end, joined by a pivot near the other end, one connected to the outer tube and the other connected to the inner tube, so that pivoting the handles relative to each other causes relative motion of the inner and outer tubes). Also, while the syringe was disclosed at a specific location relative to the endoscopic needle assembly, it will be appreciated that the syringe could be connected to the endoscopic needle assembly at other locations such that a fluid pathway is maintained between the needle and the syringe. In addition, while it is preferable that the shield have four petals, it is understood that a shield having a different number of petals, preferably between two and eight, can be used. Furthermore, while the hinges of the petals may be formed integrally with the petals, it is understood that the hinges may instead be formed separately and joined to the shield by means of adhesives, such as epoxy or cyanoacrylate, by heat-welding, or by heat-bonding with a meltable joining material, such as polyethylene, nylon, FEP or other thermoplastic. Moreover, it is understood that the disclosed elastic element encircling the petals which was designed to provide a retractive force to close the petals could be an o-ring of elastomer such as silicone rubber, urethane, ethylene-propylene, nitrile, chloroprene, or natural rubber situated in a groove or recess. Also, instead of an elastic element, it will be appreciated that a retractive force could instead be an integral function of the shield material itself as long as the material forming the shield has sufficient elastic stiffness to return the petals to their closed positions when the inner tube and needle are retracted. In addition, while a particular type of sliding seal was disclosed, a sealing device such as an o-ring, designed to maintain a fluid pathway between the needle and the syringe while sealing off the fluid pathway, could be placed inside the distal end of the inner tube and secured by plastic or metal rings pressed into the inner tube such that the rings would also act as bearings and guides for the needle as it moves in and out of the inner tube. It will therefore be appreciated by those skilled in the art that yet other modifications could be made to the provided invention without deviating from its spirit and scope as so claimed.

What is claimed is:

1. An endoscopic needle assembly, comprising:
   a) an inner tube having a proximal end, a distal end, and an interior wall defining a first lumen, said first lumen forming a fluid pathway and having a first lumen diameter;
   b) an outer tube having a proximal end, a distal end, and an interior wall defining a second lumen, said outer tube surrounding said inner tube such that said inner tube can move longitudinally relative to said outer tube within said second lumen of said outer tube;
   c) a needle connected to said distal end of said inner tube;
   d) a wire having a proximal end and a distal end and having a wire diameter smaller than said first lumen diameter of said inner tube, said distal end of said wire coupled to said interior wall of said inner tube at or adjacent said distal end of said inner tube and said proximal end of said wire connected to said inner tube along said interior wall of said inner tube at a location between said proximal end and said distal end of said inner tube, said wire providing the segment of the inner tube between the locations at which said wire is connected to said inner tube with a measure of rigidity in tension and compression; and
   e) a handle means coupled to said proximal end of said inner tube and to said proximal end of said outer tube for moving one of said inner tube and said outer tube relative to the other of said inner tube and said outer tube.

2. An endoscopic needle assembly according to claim 1, further comprising:
   f) a shield formed from a plurality of petals having proximal ends hingedly coupled to said distal end of said outer tube.

3. An endoscopic needle assembly according to claim 2, wherein:
   said shield include means for biasing said petals in a closed position.

4. An endoscopic needle assembly according to claim 1, wherein:
   at least one of said inner tube and said outer tube has a non-circular cross-section.

5. An endoscopic needle assembly according to claim 1, wherein:
   said outer tube is formed from a coil of wire surrounded by a sheath.

* * * * *